United States Patent [19]
Griesbeck

[11] Patent Number: 5,591,899
[45] Date of Patent: Jan. 7, 1997

[54] CONTINUOUSLY OPERATING INSPECTION MACHINE FOR VESSELS

[75] Inventor: Karl Griesbeck, Regensburg, Germany

[73] Assignee: Krones AG Hermann Kronseder Maschinenfabrik, Neutraubling, Germany

[21] Appl. No.: 501,268

[22] Filed: Jul. 12, 1995

Related U.S. Application Data

[63] Continuation of Ser. No. 167,796, filed as PCT/EP93/01165, May 11, 1993, abandoned.

[30]   Foreign Application Priority Data

May 11, 1992  [DE]  Germany ................ 42 14 958.4

[51] Int. Cl.$^6$ ............................................ G01M 3/32
[52] U.S. Cl. ................ 73/41; 73/49.2; 356/240; 250/223 B
[58] Field of Search ......................... 73/49.2, 865.8, 73/45.1, 45.2, 41, 45, 37; 356/240; 250/223 B; 209/523, 524, 525, 528

[56]   References Cited

U.S. PATENT DOCUMENTS

| | | |
|---|---|---|
| 3,010,310 | 11/1961 | Rowe . |
| 3,963,348 | 6/1976 | Nakatani et al. .................. 356/240 |
| 4,109,511 | 8/1978 | Powers, Jr. et al. ................ 73/45.1 |
| 4,448,526 | 5/1984 | Miyazawa ........................... 356/240 |
| 4,478,336 | 10/1984 | Thompson ......................... 356/240 |
| 4,786,801 | 11/1988 | Shay ................................ 250/223 B |
| 4,790,662 | 12/1988 | Bischkopf et al. ................. 356/240 |
| 4,852,415 | 8/1989 | Bogatzki et al. .................. 73/49.2 R |
| 4,959,537 | 9/1990 | Kimoto et al. .................... 356/240 |

FOREIGN PATENT DOCUMENTS

| | | |
|---|---|---|
| 2620046 | 4/1978 | Germany . |
| 2926592 | 5/1982 | Germany . |

OTHER PUBLICATIONS

"Sortiermaschinenanlage für Beliebig Geformte Glasbehälter", Von Knut Fischer, Glastechn. Ber. 52 (1979) Nr. 8.5., pp. 169–174.
Translation—"Sorting Equipment for Various Shapes of Glass Containers".

*Primary Examiner*—Hezron E. Williams
*Assistant Examiner*—Nashmiya Ashraf
*Attorney, Agent, or Firm*—Ryan, Maki, Mann & Hohenfeldt

[57]    ABSTRACT

Bottles made of transparent plastic material or glass are subjected to at least one stationary examination device and further for detecting impurities or damage to the bottom, side wall or mouth regions of vessels. To be able to detect defects which may cause the bottles to leak, and which cannot be detected reliably by optoelectronic devices, the vessels are inspected additionally using a leak test by developing pressures.

28 Claims, 5 Drawing Sheets

0.5 mm HOLE, SIDE WALL OF THE BOTTLE

FIG. 6

0.5 mm HOLE, BOTTOM OF THE BOTTLE

FIG. 7

3 mm HOLE

CONTINUOUSLY OPERATING INSPECTION MACHINE FOR VESSELS

This is a continuation of application Ser. No. 08/167,796, filed as PCT/EP93/01165, May 11, 1993, now abandoned.

BACKGROUND OF THE INVENTION

The invention disclosed herein relates to a continuously operating machine for inspecting vessels, especially plastic and glass bottles.

In beverage bottle plants, vessels that are contaminated, contain foreign bodies, or are damaged must be reliably detected and rejected prior to being filled with liquid. Numerous methods and apparatuses are known as in German-Offenlegungsschrift 30 36 502, German Patent 36 21 976, which permits a contactless, usually optoelectronic detection of contaminants, foreign bodies, and damage in or on bottles. Defects in returnable vessels of glass or plastic material which are used in the beverage industry cannot always be detected reliably by optoelectronic means and can only be detected with very expensive and complex methods. Some vessels may have fine hairline cracks or small holes in the bottom, side wall or mouth or areas so they cannot be refilled. This is true especially when the beverage is carbonated and the bottles are filled under counterpressure since the bottles are likely to leak and cause a slow decrease in the interior pressure as time goes on after the vessel filling operation. Defects in vessels may be caused by the thermal shock during a pre-inspection cleaning process or by force applied to the vessel during the filling operation which may be aggravated during each additional cleaning and filling cycle of a returnable bottle.

A machine described in U.S. Pat. No. 3,010,310 has been suggested for testing the resistance of glass bottles to pressure in order to detect defective bottles in a bottling line and in order to reject defective bottles. This high pressure testing machine is unsuitable for bottles or other containers having a thin wall consisting of a flexible or plastic material such as polyethylene terephthalate (PET). Moreover, a pressure test does not detect external damage to the bottle, if the defect is of a type that does not cause bottle leakage. A satisfactory system for detecting contaminants, dirt, foreign bodies, cleaning lye or liquid residues in empty bottles does not exist but is needed.

SUMMARY OF THE INVENTION

An object of the present invention is to further develop the reliability of a plastic or glass vessel inspection machine for detecting contaminated, damaged and leaking vessels at comparatively low cost and at a high production rate.

In the new inspection machine disclosed herein, vessels including plastic and glass bottles are examined for leakiness, defects, or damage which cannot be detected in a sufficiently reliable manner by optoelectronic means, or which can only be detected with a very high cost and complex machine. Whereas, on the other hand, defects, such as spots of dirt or contaminants, which cannot be detected by a leak test, are detected, in accordance with the invention, by inspection means operating in a contactless optoelectronic mode.

According to the invention, a bottle is tested for leaks by developing a comparatively low gas pressure or creating a negative pressure in the interior or the vessel. The positive or negative pressure, as the case may be, is measured for a comparatively short time. An unacceptably large pressure drop, if positive pressure is used, or a pressure increase if negative pressure is used indicates a defect in the integrity of the vessel undergoing inspection. Glass and plastic bottles are usually filled by the well-known counterpressure method. When the test is carried out with positive pressure above atmospheric pressure, the test pressure can be chosen substantially lower than the counterpressure used for pre-pressurizing the vessel which is required when carbonated beverages are bottled. The mechanical forces to which the bottles are subjected during the leak test is preferably low and, consequently, the vessels do not wear.

One advantage of the invention is that the leak test and the optoelectronic examination are carried out partly or fully simultaneously with the result that a particularly compact and cost reduced machine is achieved.

The leak test can be carried out expeditiously, especially in cases in which the bottles to be examined are axially fixed between the bottom and mouth to provide for carrying out a side wall examination wherein light is transmitted through the bottle simultaneously with performance of the leak test without any negative mutual interferences of the two examination processes occurring.

In accordance with the invention the leak test is performed concurrently with other inspection events such as detecting liquid residues in the vessel bottom by contactless optoelectronic methods. This can be easily conceived in connection with simple inspection machines which do not include any vessel side wall examination device. In this combination, a sealing disk can be pressed onto the mouth of the bottle for executing the positive or negative pressure application leak test. The sealing disk is provided with a lateral connection rather than an axial connection through which pressurized gas is supplied. Since the vessel such as a plastic or glass bottle is transparent, it is, thus, possible to transilluminate the vessel in the axial direction for the purpose of bottom inspection for liquid residue detection simultaneously with the leak test. In this case, the vessel or bottle can be held by gripping its circumferential surface or body preferably close to the neck or the mouth of the vessel so that its bottom remains clear and free.

When the leak test is performed by developing a partial vacuum or negative pressure in the vessel, the vacuum in the interior of the vessel can advantageously be restored to atmospheric pressure by introducing into the vessel carbon dioxide or sterile air, for example.

How the foregoing and other more specific objectives and features of the invention are implemented will now be described in greater detail in reference to the drawings.

DESCRIPTION OF A PREFERRED EMBODIMENT

Figure 1:
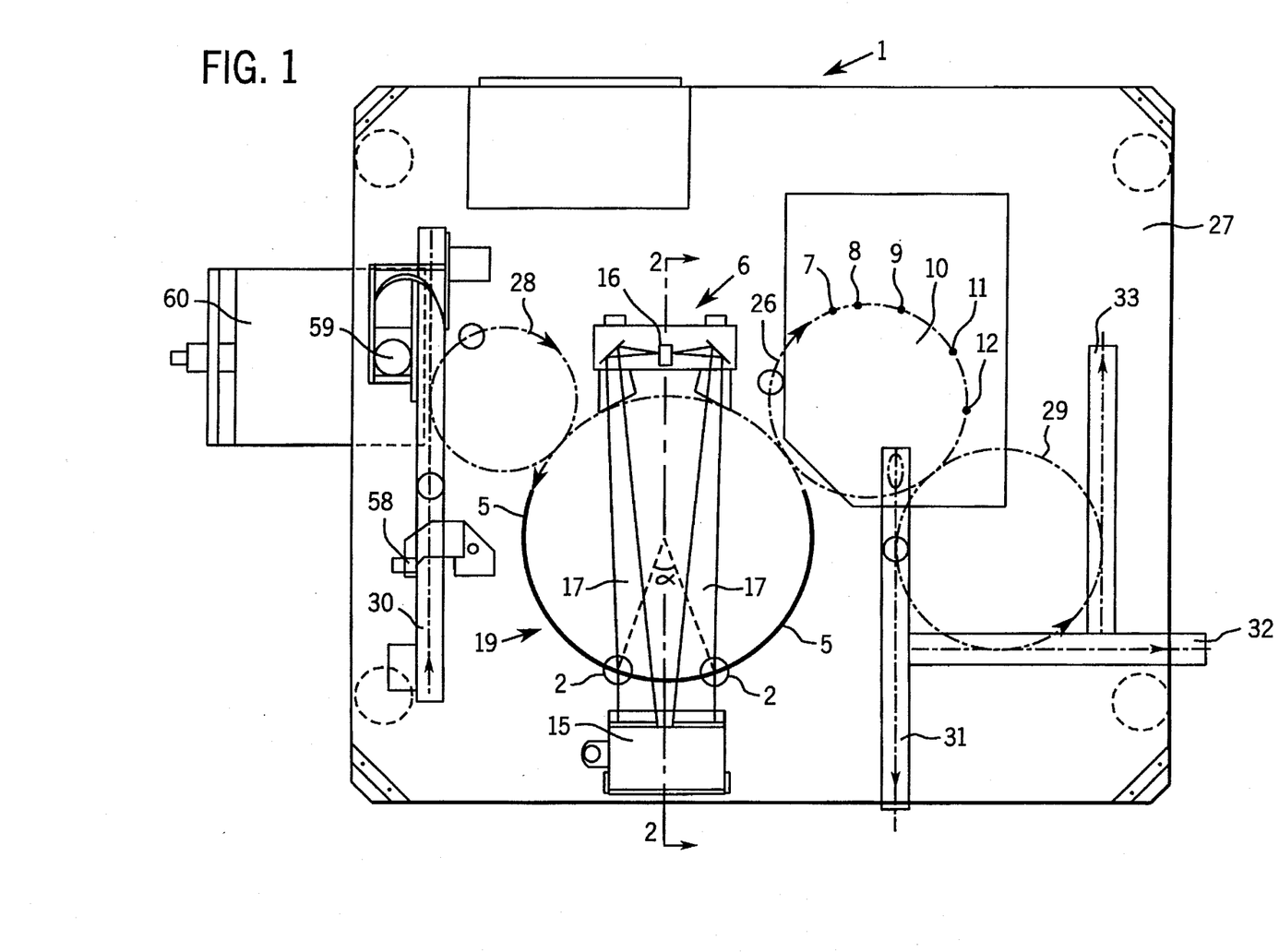
FIG. 1 is a diagrammatic top plan view of an inspection machine according to the invention.

The inspection machine shown diagrammatically in FIG. 1 comprises a table top 27 on which a first carrousel 19 is mounted for rotation about a vertical axis. In this embodiment, the vessel hereafter referred to as a bottle leak test and side wall examination of bottles are carried out on first carrousel 19. A second carrousel 26 is arranged tangentially to first carrousel 19 with the peripheries of the carrousels in contact with each other. Additional bottle inspection devices may be arranged at stationary stations along the orbit of the bottles that are transported on second carrousel 26. As viewed in the direction of bottle movement, these stations provide a bottom inspection device 7, an infrared inspection device 8 for detecting liquid residues, a decoder inspection device 9 for detecting an information code provided in the bottom of the bottle, a high frequency detection device 10 for detecting liquid residues, an orifice or mouth detection device 11 and a bottle thread inspection device 12.

A bottle infeed star wheel 28 transfers bottles from it to first carrousel 19. The second carrousel 26 is contiguous with a bottle discharge star wheel 29. The infeed star wheel 28 and the discharge star wheel 29 are equipped with selectively controllable holding members, not shown, but are well-known devices for stabilizing bottles as they are transported on the star wheel and released from it.

A side wall examination device 6 is arranged in association with the first carousel 19. The side wall examination device comprises an illumination or radiation source which is preferably a light source 15 and a sensor 16 for detecting an image projected from the bottle or other light transmitting vessel. The illumination source 15 and the sensor 16, which is a line scanning camera, are positioned outside of carrousel 19 in diametrically opposed relationship. The carousel 19 is free of built-in components in the region of the two light beam paths 17. The heavy line marked 5 defines the path along which the bottles are subjected to the leak test on first carrousel 19.

Figure 2:
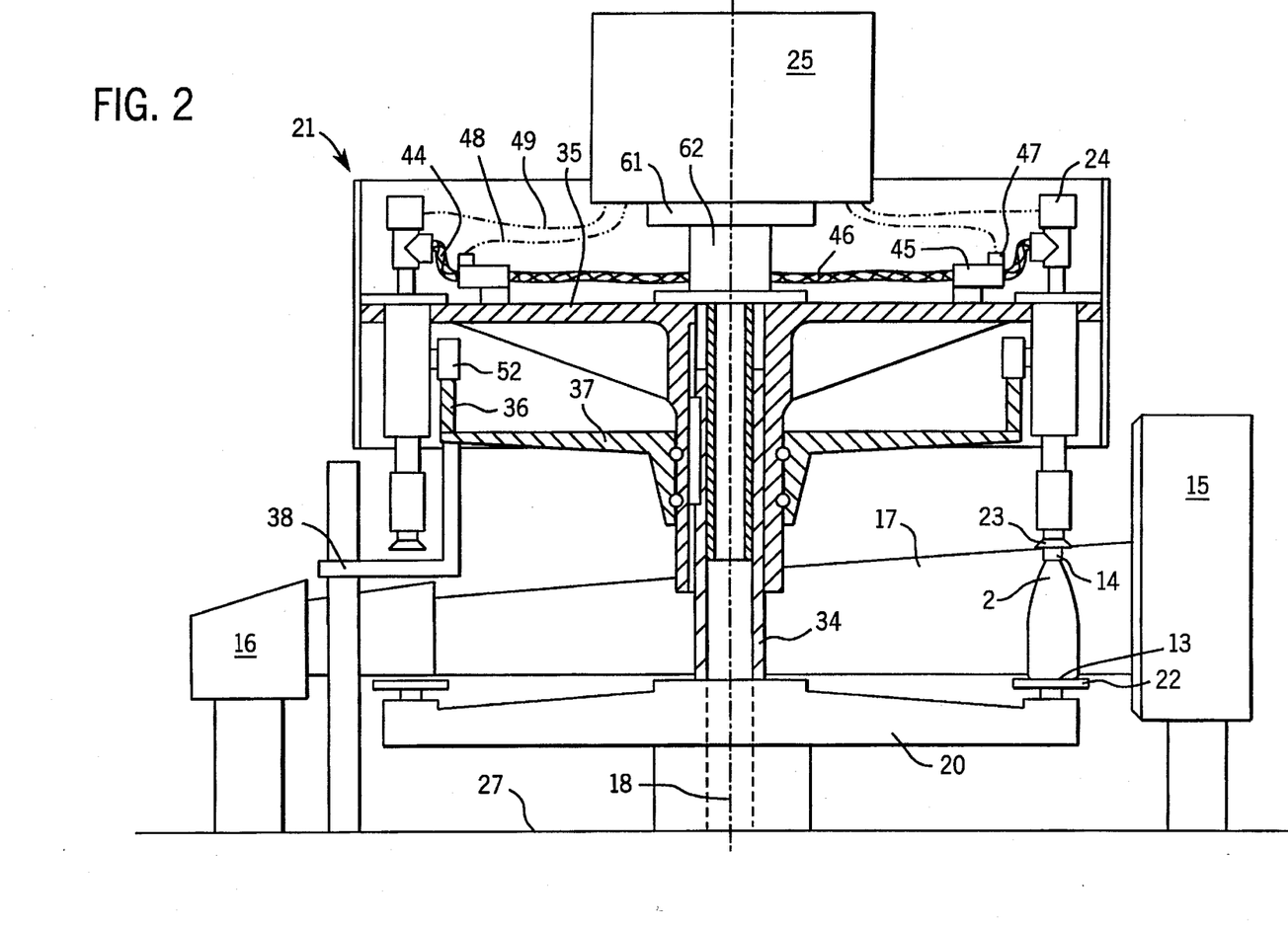
FIG. 2 is a vertical section taken on a line corresponding with 2—2 in FIG. 1.

Attention is now invited to FIG. 2 where the first carrousel 19 is shown in greater detail in a vertical section. The carrousel is comprised of a rotary table 20 which is driven rotationally about a vertical axis 18. There are rotatably driven bottle supporting disks or plates 22 mounted to rotary table 20 for supporting bottles 2, and a rotor 21 is arranged above and coaxially with rotary table 20. Rotor 21 is connected to the rotary table 20 below it through the agency of a central cylindrical column 34 which has a hollow interior. The rotor 21 is secured to rotary table 20 in a manner that causes rotary table 20 and rotor 21 to rotate together but permits rotor 21 to be adjusted vertically relative to rotary table 20 for the purpose of adapting the machine to various bottle heights. Rotor 21 comprises a radially extending plate 35 which is drivably connected or keyed to rotationally driven central hollow column 34. Uniformly spaced bottle centering heads 23 are distributed equiangularly about rotor 21. The centering heads 23 are vertically movable in a controlled manner on the outer rim of radially extending rotor plate 35. The centering and bottle stabilizing heads 23 are coaxial with the rotatable bottle support plates 22. Up and down movement of the centering heads 23 is accomplished by means of a profile cam 36 which is held in a stationary position or blocked against rotation by a fixed bracket 38 and is rigidly connected to a radially extending cam carrier or support 37. The upper side of radially extending plate 35 has secured to it a control and evaluation device 25 together with an electric circuit distributor 61 and an air diffuser 62 which will be elaborated later. The evaluation device 25 rotates together with radially extending plate 35 and with the centering heads 23 supported thereon. A supply of electric current and air to circuit distributor 61 and air diffuser 62, respectively, as well as to the evaluation device 25 is carried out from below by conductors, not shown, passing through hollow central column 34.

Figure 3:
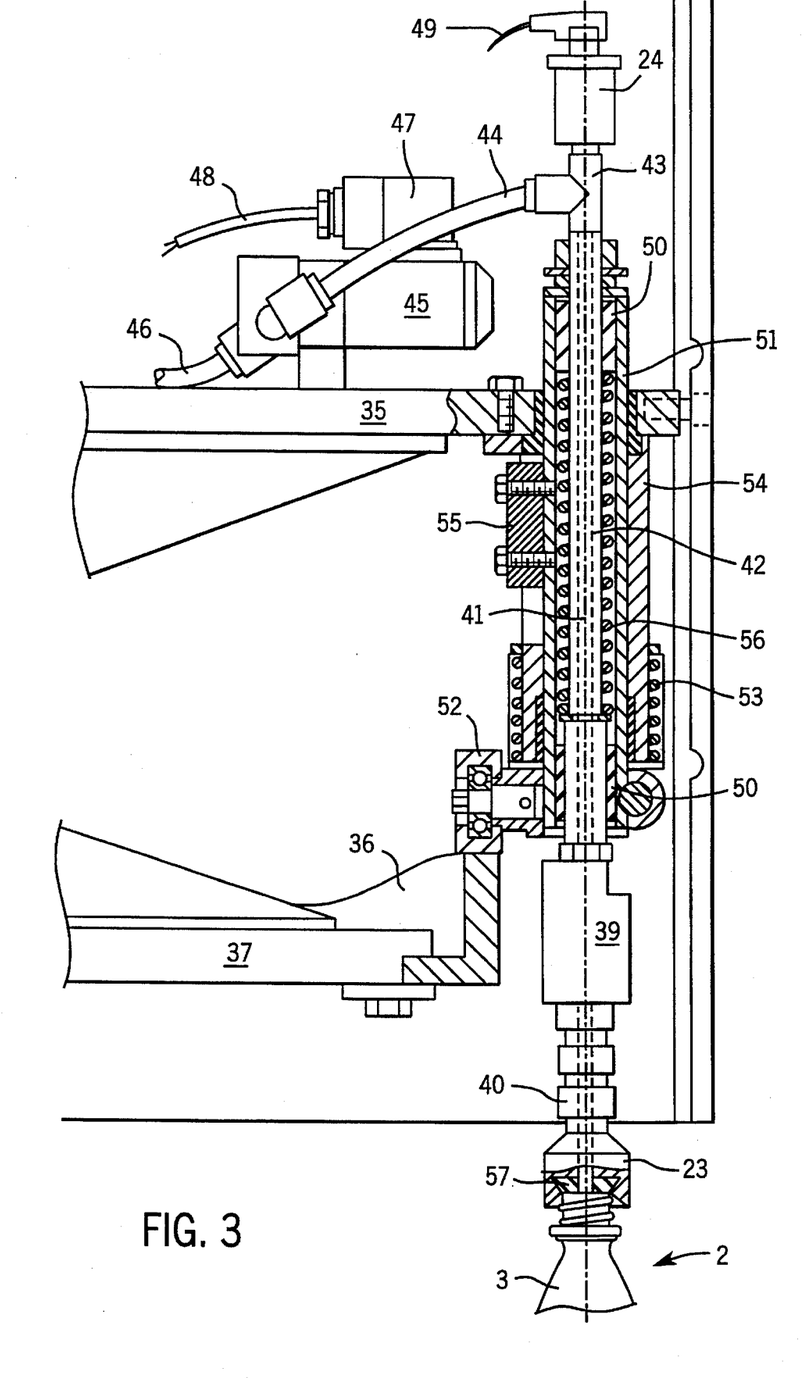
FIG. 3 is an enlarged partial vertical section through the control device for a centering head which is shown in outline in FIG. 2.
Figure 4:
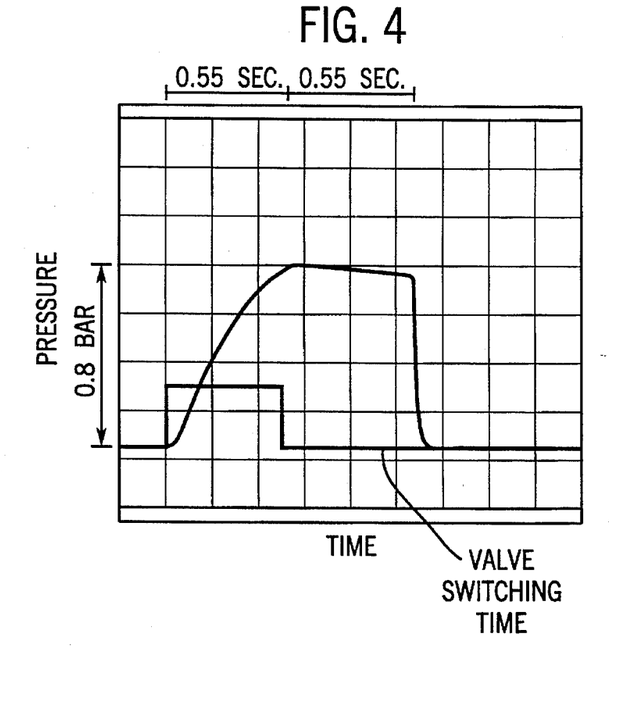
FIGS. 4–7 show pressure versus time graphs obtained during leak tests wherein the vessels have different kinds of leak tests.
Figure 5:
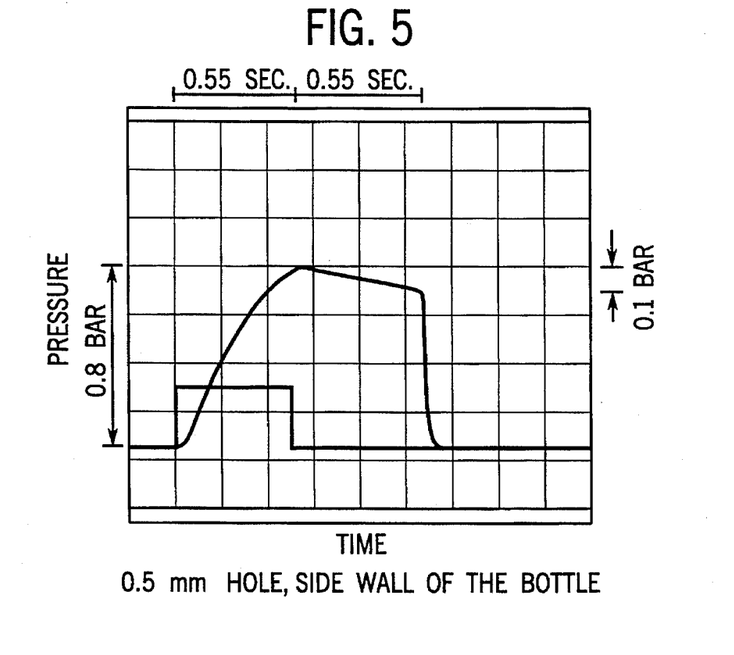
Figure 6:
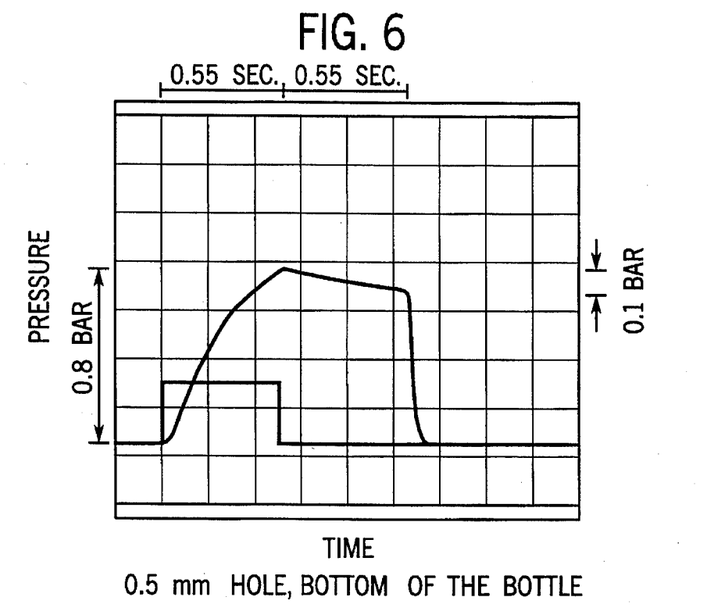
Figure 7:
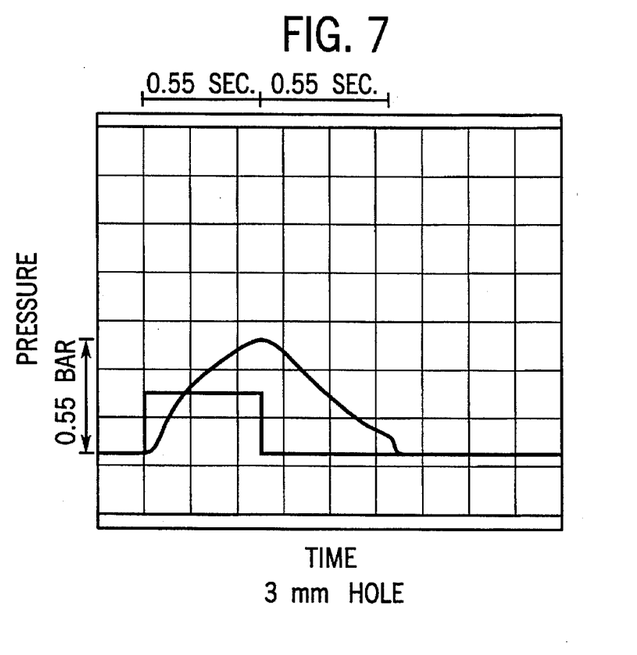

FIG. 3 shows the mechanism for controlling the vertical position of the centering heads 23. Each centering head 23 is provided with an axially extending rod 42 that supports a distributor 39 which is fixed to rod 42 and allows the bottle 2 to be rotated during inspection. Centering head 23 has a central hole 40 which extends through distributor 39 and joins a central axially extending hole 41 in rod 42. The distributor 39 is fixed to rod 42 so there is no relative rotation between the two parts. A Tee 43 is fixed to the upper end of rod 42. A gas pressure sensor 24 is connected to one branch of Tee 43. A flexible compressed air line 44 is connected to another branch of Tee 43 and extends to a compressed air controlling valve 45 which is mounted to plate 35 and is supplied with sterile compressed air through an air supply line 46 extending from air distributor 62 to compressed air valve 45. Compressed air control valve 45 is operated with an electromagnetic operator 47. Magnetic operator 47 and gas pressure sensor 24 are connected to the control and evaluation device 25 with a control line 48 and a measuring line 49, respectively.

In FIG. 3, rod 42 is guided for vertical displacement or reciprocation in a tube 51 by means of bushings 50. Tube 51 has mounted to its lower end a cam roller 52 which is biased by a spring 53 for keeping the cam roller in contact with profiled centering head lowering and lifting cam 36. Tube 51 is guided for vertical movement in a guide cylinder 54 that is rigidly connected to plate 35. Tube 51 is prevented from rotating by a block 55 which slides in a recess in guide cylinder 54. The rod 42 in the interior of tube 51 is permanently biased downwardly in the direction of bottle 2 with a spring 56. Spring 56 compensates for unavoidable height variations in bottles 2. In addition, the characteristic of pressure spring 56 guarantees that, in spite of bottle height variations, the centering seals 57 in the centering heads 23 are pressed with substantially constant pressure onto the mouth of bottles 2.

A complete inspection cycle for a bottle 2 travelling through the inspection machine will now be explained.

Referring first to FIG. 1, a bottle 2 is supplied to the inspection machine by an infeed conveyor belt 30. As is usually the case, the bottles are fed into conveyor belt 30 at equally spaced intervals with the aid of an infeed screw which is not shown but is expected to be present by persons who are familiar with bottle handling equipment. The first thing that happens after a bottle is deposited on conveyor belt 30 is for the bottle to pass a height detection camera 58 which is capable of detecting bottles that deviate from an acceptable height tolerance range. If the bottle 2 falls within the acceptable height tolerance range, a holding member, not shown, which may be a bar on the infeed star wheel 28 is activated by the height detection camera 58 and the bottle 2 is transferred from infeed conveyor belt 30 to rotary table 20 of the first carrousel 19 where the bottles are deposited on the respective rotatable support plates 22 which are shown in FIG. 2. Considering FIG. 1, bottles which have been determined to not fall within a tolerable height range by camera 58 are not seized by infeed star wheel 28, but instead, these bottles slide through a bottle chute 59 into a collecting bin 60 which is mounted to table top 27.

When a bottle 2 is transferred to a rotary table 20 of carrousel 19 by infeed star wheel 28, the bottle bottom 13 is fixed in a stable fashion on bottle supporting plate 22 as a result of a centering head 23 being lowered by lifting cam 36 as is demonstrated in FIG. 3. The electromagnetic controller 47 depicted in FIG. 3 is simultaneously activated by the control and evaluation device 25 by way of control line 48 so that compressed air valve 45 connects the air supply line 46 to compressed air line 44 to inject sterile air into the interior 3 of bottle 2 by way of Tee 43, rod 42, rotary distributor 39 and centering head 23. When pressure has maximized in the interior of bottle 2, compressed air valve 45 is closed by electromagnetic operator 47 whereupon a fixed quantity of air at a predetermined pressure is developed inside of the bottle. The evaluation means 25 then detects, by way of measuring line 49 and gas pressure sensor 24, the pressure condition prevailing in the interior 3 of bottle 2 for a specific period of time. If, during this time, evaluation device 25 detects an excessive pressure drop in the bottle, it constitutes an indication that the bottle is defective or leaking and is identified for being rejected or singled out at the exit of inspection machine 1.

While the bottle 2 is travelling in FIG. 1 along the orbital path 5 on the first carrousel 19 with the leak test in progress, side wall examination is conducted simultaneously by means of the light transmission bottle imaging method when bottle 2 passes through the beam paths 17. For this purpose, bottle 2 is gripped at its mouth 14 while being supported on plates 22 rotated about its axis at a high rotational speed along the arcuate path intercepted by the angle alpha (approximately 35°) in front of the illumination source 15, and, in the course of this procedure, the bottle is transilluminated and inspected in a narrow area along its center line throughout its entire height.

To achieve complete inspection of the main body surface of the bottle during side wall examination, the bottle is rotated about its own axis for at least 180° or by 360°, depending on the type of sensor 16 being used. The sensor 16 can be a line scanning camera or an area scanning camera, for example.

When the leak test and side wall inspection are finished, the bottle 2 is transferred to the second carrousel 26 for conducting additional inspection procedures. When the bottle arrives on carrousel 26, it is gripped in the region of its main body and in the region of its head such that its bottom and its head remain free after the centering head 23 of the first carrousel 19 had been raised by the lifting cam 36. In view of the bottle 2 being secured on carousel 26 with its bottom and its mouth being free and clear, the successive steps of inspecting the bottom, liquid residues, the bottle thread and the code can be carried out by transporting the bottle to pass stationary inspection devices 7–12. Depending on the results of the inspection, the discharge star wheel 29 is adapted for transferring the bottles to various discharge conveyor belts 31–33. For this purpose, the outfeed starwheel 29 has holding members, not shown, which can be selectively controlled to discharge bottles through any one of the discharge conveyor belts 31–33. All of the inspection processes are carried out while the bottles are transported continuously through the machine.

In accordance with the embodiment described above, the control of compressed air valve 45 by the programmable control and evaluation device 25 can be effected such that the period of time during which positive or negative pressure is developed in the bottle interior as well as the period of time used for observation of the pressure conditions remain constant independently of the instantaneous performance of the machine. Instead of using this type of control, it is, however, also possible to control the compressed air valve 45 mechanically by control cams, not shown, arranged along the orbital path of carrousel 19.

Using a 1.5 liter PET bottle for illustrative purposes, FIGS. 4–7 show various pressure versus time curves. The FIG. 4 graph shows a time versus pressure characteristic of a bottle that has no defects or leaks. The FIGS. 5–7 graphs show the effects of various defects on the pressure characteristic. For detecting these defects, an inspection pressure of 0.8 bar and an over all measurement time of 1.1 seconds, for example, suffices. Half of the measurement time is used for building the pressure in the container, and the other half is used for subsequent observation or detection of the pressure conditions prevailing in the bottle interior.

The machine described is used for inspecting bottles whose mouth or orifice does not extend at right angles to the body of the bottle.

The programmable control and evaluation device 25 is provided with a memory that stores the parameters for various sizes and types of bottles. The inspection pressure can be adjusted according to requirements.

When the leak test is conducted using vacuum in the bottle, instead of pressure, a pressure of about 80 mbars (below atmospheric pressure) proved to be particularly advantageous. It is also desirable when, after completing the leak test, carbon dioxide is introduced in the bottle through the centering head 23, for the purpose of pressure compensation, since this is of benefit to the subsequent bottle filling process. Flushing the bottles with gas, for the purpose of displacing the undesirable atmospheric oxygen, is normally carried out during PET bottle filling operations prior to introducing the liquid with which the bottle is to be filled. This allows performing the filling in a shorter period of time.

I claim:

1. A continuously operating machine for inspecting bottles made of transparent materials including glass and plastic, comprising:

a rotary table (20) rotationally driven about a vertical axis and operative to convey bottles in sequence along a predetermined arcuate path (5), a valve (45) coupled to each bottle (2) being conveyed in the sequence and controlled to open to develop in said each bottle being conveyed in the sequence a selected one of a negative pressure or a positive pressure and closed to terminate development of said selected one of a negative or positive pressure in said each bottle, and a pressure sensor (24) coupled to said each bottle being conveyed in the sequence and operative to sense the pressure in said each bottle during an interval immediately following when said valve is controlled to close and for detecting deviation from said pressure developed in said each bottle that would be indicative of a leak in said each bottle, a radiation source (15) positioned stationarily on one side of said predetermined arcuate path (5) and arranged to project a radiation beam through said each bottle (2) being conveyed in the sequence during at least a portion of the time said each bottle is conveyed over said predetermined arcuate path while undergoing detection of said deviation of pressure in said each bottle, and a radiation detector system (6) on the side opposite of said one side of said predetermined arcuate path from said radiation source (15) for intercepting an image of said each bottle being conveyed including any contaminants, foreign substance and defects in said each bottle.

2. A machine according to claim 1 wherein said radiation source (15) is a source of light and said radiation detector system (6) is sensitive to light images.

3. A machine according to claim 1 wherein said radiation beam is projected through the sidewall of said each bottle in said sequence.

4. A machine according to any one of claims 1, 2 or 3 including:
- a rotor arranged (21) for rotating about said vertical axis about which the rotary table (20) rotates in synchronism therewith the rotor being axially spaced from said rotary table,
- said rotary table (20) having mounted thereon a plurality of equiangularly spaced apart rotatably driven support plates (22) for supporting and rotating bottles (2), respectively, while the bottles are conveyed along said predetermined arcuate path (5),
- a plurality of equiangularly spaced apart bottle centering heads (23) mounted to said rotor above said support plates, respectively, said heads each comprising a movable bottle mouth (14) engaging member operable to move down to engage each bottle on each rotatable support plate, and to retract from each said bottle, to provide for releasing bottles in succession from said rotary table,
- said mouth engaging members each having a passageway communicating with each said bottle on a support plate for developing said selected one of said negative or positive pressures in each of said bottles being conveyed,
- a plurality of valves (45) mounted to said rotor, each of said valves having an inlet for coupling to a source of a selected one of said negative or positive pressure and an outlet coupled to said passageway in said each of said mouth engaging members, and
- a plurality of pressure sensors for sensing pressure, respectively, in said each of the bottles on support plates when engaged, respectively, by said mouth engaging members, said pressure sensors producing signals, respectively, representative of the pressure in said each bottle when said mouth of said each bottle is engaged.

5. A machine according to claim 4 including, an evaluation device (25) mounted to said rotor (21) and adapted to receive a signal corresponding to the pressure in said each bottle for evaluating the pressure in said each bottle being conveyed within a time interval following termination of the development of said selected one of a negative or positive pressure in said each bottle.

6. A machine according to claim 5 including:
- an infeed star wheel from which bottles are transferred successively to said rotating bottle support plates when the plates are positioned, respectively, by said rotary table (20) at a predetermined rotational angle of the table,
- a rotating carrousel (26) to which said each bottle being conveyed is discharged from the rotary table after being inspected, the angle of rotation of the rotary table (20) from where said each bottle is transferred to said table to where said each bottle is discharged from the table is at least 180 degrees.

7. A machine according to claim 4 including:
- a cam follower roller (52) mounted to each centering head,
- a profile cam (36) fixedly mounted concentrically with the axis of rotation of the rotor and rotary table (20) on which each of said followers run to raise and lower said centering heads (23) at predetermined angular positions of the rotary table.

8. A machine according to claim 6 including:
- at least one bottle inspection device, arranged around said carrousel (26) for performing at least one inspection operation on said each bottle on said carrousel (26) as said each bottle passes said inspection device.

9. A machine according to claim 4 including:
- coaxial shaft members (34) to which said rotor (21) and said rotary table (20) are affixed for rotating together with a clear space on opposite sides of said shaft members, said radiation source projecting beams to said radiation detector system through said each bottle and the clear space on opposite sides of said shaft members.

10. A machine according to claim 8 including means on said carrousel (26) for supporting said each bottle for rotation such that the bottom (13) of said each bottle remains unobstructed and there are a plurality of bottle inspection devices arranged around the carrousel.

11. A machine according to claim 8 wherein said at least one bottle inspection device is a device selected from the class consisting of devices for examining the bottom of said each bottle, thread on said each bottle and residue in said each bottle.

12. A machine according to claim 4 including:
- a source (46) of gas coupled to said each bottle being conveyed and means (45) controlled to admit pressurized gas to said each bottle being conveyed when negative pressure exists in said each bottle being conveyed after testing for leaks and after imaging said each bottle being conveyed is completed.

13. A machine according to claim 12 wherein said gas is one selected from the group of carbon dioxide and sterile air.

14. A continuously operating machine for inspecting bottles made of glass or plastics, comprising:
- a conveyor and an infeed station where bottles are transferred to said conveyor in sequence and an outfeed station where bottles are discharged from said conveyor,
- means for developing a selected one of a negative or positive pressure in each bottle while being conveyed and a pressure testing device operative to test the pressure in said each bottle for a change indicative of a leak,
- a light source positioned proximate to said conveyor from which a light beam is projected to impinge on at least a part of said each bottle and a detector positioned for detecting said light beam as altered by foreign matter and defects on and in said part of said each bottle during a time interval which overlaps at least in part the time during which said each bottle is tested for a leak.

15. A continuously operating machine for inspecting bottles made of glass and plastics, comprising:
- a turntable rotatably driven about a vertical axis and adapted for receiving bottles in sequence and transporting each bottle along a circular path,
- a source of light from which a light beam is projected that impinges on at least a part of said each bottle in said sequence while said each bottle is being transported along said path, and a detector arranged for detecting said light as altered by foreign matter and defects on and, in said part,
- a device operative to couple said each bottle to a selected one of a negative pressure or a positive pressure source while said each bottle is being transported along said path and concurrently with said detecting of light in said each bottle, and a pressure sensor coupled to said each bottle to detect pressure existing in said each bottle following development of said pressure to determine if said each bottle has a leak.

16. A machine according to any one of claims 14 or 15 wherein:

said light source is positioned for projecting said light beam to impinge on and be transmitted through said each bottle being transported in said sequence and said detector is positioned on a side of said each bottle opposite of where said light beam impinges for detecting the light beam as altered by the sidewall of said each bottle.

17. A machine according to claim 15 including:

an infeed station at which said turntable receives said each bottle in sequence and an outfeed station at which said each bottle is discharged from said turntable, said light source is positioned adjacent said circular path at an angle of rotation of said turntable where said each bottle is under pressure as said each bottle passes through said beam projected from said light source.

18. A machine according to claim 14 including a plurality of rotationally drivable bottle support devices on said conveyor to which said each bottle is transferred in sequence as said turntable rotates past said infeed station, and said each bottle is rotated with said support devices about the axis of said each bottle at least through an angle of 180° while said each bottle is passing through said light beam.

19. A machine according to claim 15 wherein:

said turntable is provided with a plurality of circumferentially spaced apart rotatable bottle support plates on which said each bottle is received in sequence, a rotor is arranged above said turntable and coaxially therewith for said rotor and turntable to rotate in synchronism, rotatably driven bottle centering heads on said rotor, one centering head positioned above each said bottle support plate, and means for lowering said centering heads to grip and clamp said each bottle as said each bottle is received, on said plates and for raising the respective centering head to release the grip on said each bottle before said each bottle is discharged from said turntable.

20. A machine according to claim 19 wherein:

said gas pressure sensor is mounted to each centering head for sensing the pressure in said each bottle that is clamped by a head and operative to produce a signal representative of the pressure in said each bottle, and an evaluation device mounted on said rotor operative to measure said signal from each pressure sensor.

21. A machine according to any one of claims 15, 17, 19 or 20 including:

a carrousel (26) driven rotationally and arranged to receive said each bottle that has been inspected on and is discharged from said turntable, said carrousel transporting said bottles along a circular path with the bottom of said each bottle exposed, a plurality of bottle inspection devices arranged stationarily along said circular path, said inspection devices selected from a class consisting of a bottle bottom, a bottle mouth, mouth screw thread and residual liquid in said bottle inspecting devices.

22. A machine for inspecting bottles made of plastics or glass comprising:

a rotationally driven turntable for transporting said bottles in sequence along a circular path between an infeed station where said bottles are deposited on said turntable and a discharge station where said bottles are discharged from said turntable, devices for pressurizing each bottle positively or negatively and for concurrently inspecting each bottle for a leak as said each bottle is transported along said path, and an optoelectronic inspection apparatus arranged stationarily along said circular path and adapted for inspecting said each bottle for the presence of foreign matter and damage concurrently with said each bottle undergoing a test for a leak as said each bottle passes said optoelectronic inspection apparatus.

23. A method of inspecting plastic and glass bottles, comprising the steps of:

transporting bottles on a turntable between an infeed station where said bottles are transferred to the turntable and an outfeed station where said bottles are removed from the turntable, developing in each bottle after said each bottle is fed to the turntable a selected one of a negative or a positive pressure, and when said each bottle has pressure, testing the pressure in said each bottle for a change indicative of a leak in said each bottle, and during an interval while said each bottle is being transported between said stations and being tested for a leak, inspecting said each bottle for damage and the presence of foreign matter using optoelectronic inspection apparatus positioned proximate to the turntable.

24. A method according to claim 23 including the step of determining the rate at which pressure in said each bottle changes when said pressure is developed.

25. A method according to claim 23 including the steps of:

terminating development of pressure in said each bottle and detecting the gas pressure gradient during a settable measuring interval.

26. A method according to claim 25 including the step of:

holding the length of time for developing pressure in said each bottle constant independently of the speed at which said bottles are transported.

27. A method according to claim 25 including the step of:

holding said interval for detecting pressure gradient independent of the speed at which said bottles are transported.

28. A method according to claim 23 including the steps of rotating said each bottle about a vertical axis through an angle of at least 180° while said each bottle is being inspected for damage or for the presence of foreign matter.

* * * * *

UNITED STATES PATENT AND TRADEMARK OFFICE
CERTIFICATE OF CORRECTION

PATENT NO. : 5,591,899
DATED : January 7, 1997
INVENTOR(S) : Griesbeck

It is certified that error appears in the above-indentified patent and that said Letters Patent is hereby corrected as shown below:

Column 7 (Claim 7) Line 64   After "said" insert --- cam ---

Signed and Sealed this

First Day of July, 1997

Attest:

BRUCE LEHMAN

*Attesting Officer*   *Commissioner of Patents and Trademarks*